US012285394B2

(12) United States Patent
Kerr et al.

(10) Patent No.: US 12,285,394 B2
(45) Date of Patent: Apr. 29, 2025

(54) KETOGENIC COMPOUNDS, COMPOSITIONS, METHODS AND USE THEREOF

(71) Applicant: 9500-0535 QUEBEC INC., Montreal (CA)

(72) Inventors: Steve Kerr, Boucherville (CA); Mylvaganam Murugesapillai, Toronto (CA); Alex Millin, Toronto (CA)

(73) Assignee: 9500-0535 Québec Inc., Boucherville (CA)

( * ) Notice: Subject to any disclaimer, the term of this patent is extended or adjusted under 35 U.S.C. 154(b) by 19 days.

(21) Appl. No.: 18/072,747

(22) Filed: Dec. 1, 2022

(65) Prior Publication Data

US 2023/0095764 A1 Mar. 30, 2023

Related U.S. Application Data

(63) Continuation of application No. 17/251,440, filed as application No. PCT/CA2019/050777 on Jun. 4, 2019, now abandoned.

(60) Provisional application No. 62/683,817, filed on Jun. 12, 2018.

(30) Foreign Application Priority Data

Nov. 1, 2018 (CA) .................................. CA 3022995

(51) Int. Cl.
| | |
|---|---|
| *A61K 31/19* | (2006.01) |
| *A61K 9/06* | (2006.01) |
| *A61K 31/047* | (2006.01) |
| *A61K 47/61* | (2017.01) |

(52) U.S. Cl.
CPC ............... *A61K 31/19* (2013.01); *A61K 9/06* (2013.01); *A61K 31/047* (2013.01); *A61K 47/61* (2017.08)

(58) Field of Classification Search
CPC ........ A61K 31/19; A61K 9/06; A61K 31/047; A61K 47/61; A61K 31/722; A61K 47/36; A61K 47/38; A61K 31/717; C08J 2301/28; C08J 2305/08; C08J 3/075; A61P 3/04; A61P 3/10; A61P 21/00; A61P 25/28; A61P 35/00; A61P 25/00; C08B 15/005; C08B 37/003; C08B 15/04; C08L 1/286; C08L 5/08
See application file for complete search history.

(56) References Cited

U.S. PATENT DOCUMENTS

| | | | |
|---|---|---|---|
| 3,623,237 A | 11/1971 | Whittaker | |
| 6,323,237 B1 | 8/2001 | Veech | |
| 8,642,654 B2 | 2/2014 | Clarke et al. | |
| 9,138,420 B2 | 9/2015 | D'Agostino et al. | |
| 10,051,880 B2 | 8/2018 | Clarke et al. | |
| 2003/0022937 A1 | 1/2003 | Veech | |
| 2010/0041751 A1 | 2/2010 | Henderson | |
| 2010/0137236 A1* | 6/2010 | Ganapathy | A61P 1/00 514/356 |
| 2013/0102663 A1 | 4/2013 | Clarke | |
| 2014/0350105 A1* | 11/2014 | D'Agostino | A61K 31/22 514/547 |
| 2016/0206773 A1 | 7/2016 | Mousa et al. | |
| 2017/0258745 A1 | 9/2017 | Millet | |
| 2018/0021274 A1 | 1/2018 | Arnold | |
| 2018/0177906 A1 | 6/2018 | Sugiura | |
| 2021/0275475 A1 | 9/2021 | Kerr et al. | |

FOREIGN PATENT DOCUMENTS

| | | |
|---|---|---|
| CA | 2734720 A1 | 2/2010 |
| CN | 102164884 A | 8/2011 |
| CN | 105050594 A | 11/2015 |
| EP | 2539312 B1 | 2/2011 |
| JP | 2013-520454 A | 6/2013 |
| RU | 2426535 C2 | 8/2011 |
| WO | 2000004895 | 2/2000 |
| WO | 2000004895 A2 | 2/2000 |
| WO | 2014/153416 A1 | 9/2014 |
| WO | 201453416 A1 | 9/2014 |
| WO | 2016/199756 | 12/2016 |
| WO | 2016/199756 A1 | 12/2016 |
| WO | 2017/221268 A1 | 12/2017 |

OTHER PUBLICATIONS

Sacco et al. Gels. 2018; 4(67): pp. 1-29. (Year: 2018).*
Li et al. Food Hydrocolloids. 2017; 62: 222-229. (Year: 2017).*
Office Action in Japanese Application No. 2020-569867, dated May 31, 2023, with English translation (10 pages).
Kashiwaya Y, Takeshima T, Mori N, Nakashima K, Clarke K, Veech RL. (2000). D-beta-hydroxybutyrate protects neurons in models of Alzheimer's and Parkinson's disease. Proc Natl Acad Sci U S A, 97(10):5440-4.
Veech RL. (2013) Ketone esters increase brown fat in mice and overcome insulin resistance in other tissues in the rat. Ann N Y Acad Sci,1302, 42-48.
Veech, RL. (2014) Ketone ester effects on metabolism and transcription. J Lipid Res, 55(10), 2004-2006.

(Continued)

*Primary Examiner* — David Browe
(74) *Attorney, Agent, or Firm* — Thrive IP®; Jeremy M. Stipkala

(57) ABSTRACT

The present disclosure is directed to a method for increasing ketone levels in the bloodstream of a subject comprising administering to the subject an aqueous composition comprising a hydrogel, the hydrogel comprising:

β-hydroxybutyric acid (BHB); and carboxymethylcellulose or chitosan;

wherein the BHB and the carboxymethylcellulose or chitosan form a hydrogel matrix, and the matrix has a pH in the aqueous composition of about 4.0±0.5.

10 Claims, No Drawings

(56) References Cited

OTHER PUBLICATIONS

Hertz, L., Chen, Y., & Waagepetersen, H. S. (2015). Effects of ketone bodies in Alzheimer's disease in relation to neural hypometabolism, ß-amyloid toxicity, and astrocyte function. Journal of Neurochemistry, 134(1), 7-20.
Youm, Y.-H., Nguyen, K. Y., Grant, R. W., Goldberg, E. L., Bodogai, M., Kim, D., Dixit, V. D. (2015). The ketone metabolite ß-hydroxybutyrate blocks NLRP3 inflammasome-mediated inflammatory disease. Nature Medicine, 21(3), 263-269.
Samoilova, M., Weisspapir, M., Abdelmalik, P., Velumian, A. A., & Carlen, P. L. (2010). Chronic in vitro ketosis is neuroprotective but not anti-convulsant. Journal of Neurochemistry, 113(4), 826-835.
Newman, J. C., & Verdin, E. (2014). Ketone bodies as signaling metabolites. Trends in Endocrinology and Metabolism, 25(1), 42-52.
White, H., & Venkatesh, B. (2011). Clinical review: Ketones and brain injury. Critical Care, 15(219), 1-10.
Cox, P. J., & Clarke, K. (2014). Acute nutritional ketosis: implications for exercise performance and metabolism. Extreme Physiology & Medicine, 3(1), 17.
Poff, A. M., Ari, C., Arnold, P., Seyfried, T. N., & D'Agostino, D. P. (2014). Ketone supplementation decreases tumor cell viability and prolongs survival of mice with metastatic cancer. International Journal of Cancer, 135(7), 1711-1720.
Prins, M. L. (2008). Cerebral Metabolic Adaptation and Ketone Metabolism after Brain Injury. Journal of Cerebral Blood Flow & Metabolism, 28(1), 1-16.
Gasior, M., Rogawski, M. A., & Hartman, A. L. (2006). Neuroprotective and disease-modifying effects of the ketogenic diet. Behavioural Pharmacology, 17(5-6), 431-9.
Yamada, T., Zhang, S .- J., Westerblad, H., & Katz, A. (2010). {beta)-Hydroxybutyrate inhibits insulin-mediated glucose transport in mouse oxidative muscle. American Journal of Physiology. Endocrinology and Metabolism, 299(3), E364-73.
Arakawa, T., Goto, T., & Okada, Y. Effect of ketone body (d-3-hydroxybutyrate) on neural activity and energy metabolism in hippocampal slices of the adult guinea pig. Neuroscience Letters (1991).
Kumar Dutta, P., Dutta, J., & Tripathi, V. S. . Chitin and chitosan: Chemistry, properties and applications. Journal of Scientific & Industrial Research (2004).
Wensvoort, J., Kyle, D. J., Orskov, E. R., & Bourke, D. A. . Biochemical adaptation of camelids during periods where feed is withheld. Rangifer (2001).
Lincoln, B. C., Rosiers, C. Des, & Brunengraber, H. Metabolism of S-3-hydroxybutyrate in the perfused rat liver. Archives of Biochemistry and Biophysics (1987).
Murphy, J. J., Bastida, D., Paria, S., Fagnoni, M., & Melchiorre, P. Asymmetric catalytic formation of quaternary carbons by iminium ion trapping of radicals. Nature (2016).
Sena, S. F. Beta-hydroxybutyrate : New Test for Ketoacidosis. Department of Pathology and Laboratory Medicine, (2010).
Laeger, T., Metges, C. C., & Kuhla, B. Role of ß-hydroxybutyric acid in the central regulation of energy balance. Appetite (2010).
Extended European Search Report dated Feb. 14, 2022, EP Application No. 19820603.9 (9 pages).
Mark Evans et al., "Effect of acute ingestion of ß-hydroxybutyrate salts on the response to graded exercise in trained cyclists," European Journal of Sport Science, 2018, vol. 18, No. 3, 376-86.
Waleed Faisal et al., "Taste Masking Approaches For Medicines," Current Drug Delivery, 2018, vol. 15, No. 2, 167-85.
Noriaki Funisaki et al., "Masking Mechanisms of Bitter Taste of Drugs Studied with Ion Selective Electrodes," Chem. Pharm. Bull., 2006, vol. 54, No. 8, 1155-61.

David A. Holdsworth et al. "A Ketone Ester Drink Increases Postexercise Muscle Glycogen Synthesis in Humans," Medicine & Science in Sports & Exercise, 2017, vol. 49, No. 9, 1789-95.
Li et al. "Effect of substitution degree on carboxymethylcellulose interaction with lysozyme," Food Hydrocolloids, 2017, vol. 6, pp. 222-229.
Silvestri et al. "A poly(3-hydroxybutyrate)-chitosan polymer conjugate for the synthesis of safer gold nanoparticles and their applications," Green Chem., 2018, vol. 20, pp. 4975-4982.
International Search Report for PCT/CA2019/050777 (Aug. 20, 2019) (4 pages).
Written Opinion for PCT/CA2019/050777 (Aug. 20, 2019) (6 pages).
Google translation of Office Action in Chinese corresponding application No. 2019800421694, dated May 22, 2023 (9 pages).
Google.com English translation of Chinese Application No. CN 105050594A (24 pages).
Google.com English translation of Chinese Application No. CN 102164884A (21 pages).
Office Action in Korean application No. 10-2020-7036282, dated Jun. 10, 2024 (6 pages).
Google Machine Translation of Office Action in Korean application No. 10-2020-7036282, dated Jun. 10, 2024 (6 pages).
Examination Report for Australian Application No. 2019284234, dated Mar. 28, 2024 (3 pages).
Google Machine Translation of Russian application No. RU2426535, dated Aug. 20, 2011 (24 pages).
Office Action in Canadian application No. 3,022,995, dated Jan. 2, 2019 (5 pages).
Office Action in Canadian application No. 3,022,995, dated Feb. 20, 2019 (3 pages).
Google Machine Translation of first Office Action in Chinese application No. 201980042169.4 dated May 22, 2023 (9 pages).
Office Action in Japanese application No. 2020-569867, dated Jun. 2, 2023 (4 pages).
Google Machine Translation of Office Action in Japanese application No. 2020-569867, dated Jun. 2, 2023 (6 pages).
Evans, Mark et al., "Effect of acute ingestion of [beta]-hydroxybutyrate salts on the response to graded exercise in trained cyclists.", European Journal of Sport Science vol. 18, No. 3, Apr. 2018 (Apr. 2018), pp. 376-386.
Faisal, Waleed et al., "Taste Masking Approaches for Medicines", Current Drug Delivery, vol. 15, No. 2, Feb. 14, 2018 (Feb. 14, 2018), pp. 167-185.
Funasaki, Noriaki at al., "Masking mechanisms of bitter taste of drugs studied with ion selective electrodes", Chemical & Pharmaceutical Bulletin (Tokyo), vol. 54, No. 8, Aug. 2006, pp. 1155-1161.
Holdsworth, David A. et al., "A Ketone Ester Drink Increases Postexercise Muscle Glycogen Synthesis in Humans", Medicine and Science in Sports and Exercise, vol. 49, No. 9, Sep. 1, 2017 (Sep. 1, 2017), pp. 1789-1795.
English translation of Japanese application No. 2013/520454, dated Jun. 6, 2013 (24 pages).
First Examination Report for Indian Application No. 202047054029, dated Jul. 24, 2023 (7 pages).
European Supplementary Search Report for European Application No. 19820603.9, dated Feb. 14, 2022 (9 pages).
Office Action in Russian application No. 2020143536, dated May 30, 2024 (12 pages).
English translation of Office Action in Russian application No. 2020143536, dated May 30, 2024 (7 pages).
Second Office Action in Chinese application No. 201980042169.4 dated Dec. 6, 2023 (7 pages).
English translation of Second Office Action in Chinese application No. 201980042169.4 dated Dec. 6, 2023 (10 pages).

\* cited by examiner

KETOGENIC COMPOUNDS, COMPOSITIONS, METHODS AND USE THEREOF

CROSS-REFERENCE TO RELATED APPLICATIONS

This application is a continuation of and claims the benefit of priority to U.S. non-provisional patent application Ser. No. 17/251,440, filed on Dec. 11, 2020, which represents the U.S. National Phase under 35 U.S.C. § 371 of International Patent Application No. PCT/CA2019/050777 filed Jun. 4, 2019, which in turn claims benefit of Canadian Patent Application No. 3,022,995 (allowed), filed Nov. 1, 2018, and U.S. Provisional Application No. 62/683,817, filed Jun. 12, 2018, the contents of which are incorporated herein by reference in their entirety.

FIELD

The present disclosure relates to novel ketogenic compounds comprising β-hydroxybutyric acid and a weakly basic polymer and compositions of such compounds. The disclosure also includes methods for inducing nutritional ketosis comprising administering the compounds or compositions to a mammal in need thereof or use of such compounds or compositions as an alternative energy substrate.

INTRODUCTION

Increasing ketone levels in the blood stream or tissues can mainly be achieved by nutritional methods like the ketogenic diet (KD) or the ingestion of exogenous ketone supplements. However, severe compliance issues as well as health concerns with the KD are well documented in the scientific literature and the use of currently available supplements is still limited. In fact, given the extreme unpalatability and rapid absorption of 3-hydroxybutyric acid (β-hydroxybutyric acid, BHB), the vast majority of commercially available ketone supplements use salts of BHB, such as sodium, calcium and potassium salts, to improve palatability and regulate the absorption of BHB, but the recommended daily allowance for these mineral ions, which are well established, severely limits the total amount of BHB-salts which can be ingested. While some supplements rather rely on ketone esters to regulate the absorption of BHB, palatability remains an important restricting factor.

Ketone bodies are naturally elevated to serve as alternative energy substrate during prolonged reduction of glucose availability as in fasting, starvation and intense exercise or due to insufficient insulin production as in type-1 diabetes. The scarcity of glucose triggers a metabolic shift towards fatty acid oxidation and hepatic ketogenesis, elevating the blood concentration of ketone bodies acetoacetate (AcAc) and beta-hydroxybutyrate (BHB).

In the 1920s, researchers developed a fat based diet that induces that same metabolic shift without the need for calorie restriction. The ketogenic diet (KD), as it is known, has since been used as a non-pharmaceutical treatment of pediatric epilepsy. Medical research supports the prevention or therapeutic potential of the KD for a broad range of medical conditions such as traumatic brain injuries, neurodegenerative disorders, strokes, Alzheimer's disease, cancer, amyotrophic lateral sclerosis (ALS), type-2 diabetes, obesity, Parkinson's disease, oxidative stress, etc. (see references).

Amongst others, elevation of ketone bodies in blood have been shown to improve glycemic control, to suppress inflammation, to decrease mitochondrial reactive oxygen species (ROS) production and favorably alter mitochondrial bioenergetics. Ketone bodies increase the hydraulic efficiency of the heart, simultaneously decreasing oxygen consumption while increasing ATP production. Thus, elevated ketone bodies increase metabolic efficiency and as a consequence, reduce superoxide production and increase reduced glutathione. From a neurological perspective, one of the mechanism by which ketone bodies achieves their potential is through the biochemical process of their energy metabolism. During cellular respiration in the mitochondria, glucose enters the stand citric acid cycle, which in many brain disease or trauma situations is interrupted or impaired. Ketone bodies enter the citric acid cycle at a different step and thus rescue the energy metabolism of the cell.

Despite such potential, some factors limit the use of this metabolic therapy for an extensive clinical use. The main limitation appears to be patient compliance given KD's severe dietary restriction. The classical KD requires that 80 to 90% of the total caloric intake of an individual be derived from fat, making it perceived as unpalatable by the vast majority of users. Also, maintaining a state of nutritional ketosis can be quite challenging as the consumption of even a small quantity of carbohydrates or protein can rapidly inhibit ketogenesis. Nutritional ketosis also requires an adaptation period for the system to optimize the production of ketone bodies and utilization. It can take several weeks for patients to adapt to KD and they may experience undesirable symptoms during this transition. Amongst others, long term KD side effects may include constipation, dyslipidemia, dysmenorrhea, slowed or stunted growth in children, kidney stones, etc. Finally, supplements are almost systematically necessary to counter the dietary deficiency of many micronutrients.

The promising health potential of nutritional ketosis has given rise to exploring suitable alternatives to the KD. Several recent studies have shown similar results in using exogenous ketone supplements instead of KD, without the extreme dietary restrictions. The most trivial way to achieve oral nutritional ketosis would appear to be the ingestion of pure BHB or acetoacetic acid (AcAc). However, given the extreme palatability issue and rapid absorption rate of these compounds, their use is consensually recognised as impractical. AcAc is also an unstable acid, like many other members of its class.

Current available ketogenic oral supplements consist of either medium chain triglyceride oil (MCT) (see for example, U.S. Pat. No. 9,138,420), BHB mineral salts and ketone body esters. Each of these supplements have their own limitations and implications. For instance, the use of MCT has been reported to cause gastrointestinal distress in the vast majority of patients unless ingested in small doses which fairly restricts its effectiveness. As mentioned, the ingestion of BHB mineral salts is also limited by the allowed daily intake of the accompanying mineral to avoid potentially damaging or even lethal mineral overload. The osmotic balance of the system is also impacted. As for ketone body esters, they are novel molecules where two or more ketone bodies such as BHB and AcAc are linked through a covalent bond. These prodrugs modify the natural structure of ketone bodies, so their usage is restricted and further clinical trial need to be performed to assess their safety. Also, their palatability has been reported by early users at best as tolerable, but certainly not suited for mass market daily consumption.

SUMMARY

The present disclosure relates to novel compounds comprising β-hydroxybutyric acid (BHB) and at least one weakly basic polymer. In further embodiments, the present disclosure includes novel compounds comprising BHB, and at least one indigestible weakly basic polymer, which when dissolved in water, forms a hydrogel-matrix that provides many advantages: (1) repulsive taste of BHB is neutralized, (2) additional ketogenic precursors can be incorporated in the matrix forming a hydrogen-bonding network that keeps neutralizing the repulsive taste of such precursor, (3) contrary to mineral salts, the accompanying polymer is not absorbed by the system and thus only BHB and other precursors are absorbed by a subject.

Accordingly, in one embodiment of the disclosure, there is included compounds comprising:
(i) 3-hydroxybutyric acid (β-hydroxybutyric acid); and
(ii) a weakly basic polymer comprising weak base functional groups.

In one embodiment, the weakly basic polymer comprises weak-base functional groups, and the molar ratio between the weak-base functional groups and the BHB in the compound is about 1:1. In some embodiments, the compounds comprising BHB and the weakly basic polymer are weak-acid weak-base salt compounds (ionic compounds) or weak-acid weak-base buffered salt compounds.

In further embodiments, the present disclosure includes aqueous compositions comprising the compounds as a hydrogel matrix, wherein the hydrogel matrix incorporates additional BHB, including dimers, trimers, tetramers and oligomers of BHB, polymers of BHB, 1,3-butanediol and/or acetoacetic acid or esters thereof, into the matrix, such that the additional compounds do not escape from the matrix.

The present disclosure is also directed to methods for inducing nutritional ketosis in a mammal in need thereof, the method comprising administering to a mammal an effective amount of a compound of the disclosure or composition comprising the compound.

The present disclosure also includes kits comprising a compound of the disclosure in one container, and water or an aqueous solution in a second container, an instructions for use, wherein the user combines the compound with water or the aqueous solution to form the hydrogel matrix.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DESCRIPTION OF VARIOUS EMBODIMENTS

Definitions

The term "weakly basic polymer" as used herein refers to a polymer having a backbone which contains one or more weakly basic monomer units, and has, for example, a pKb in the range 4.0 to 10.5. The weakly basic polymer may also be a co-polymer, wherein certain monomers do not possess weakly basic functional groups.

The term "weakly basic monomer units" refers to monomers used to form the weakly basic polymers, where the monomer unit possesses weakly basic functional groups.

The term "weak base" or "weakly basic" as used herein in the context of a weak base functional group refers to a group, moiety or other chemical structure that only partially ionizes water as shown in the following scheme.

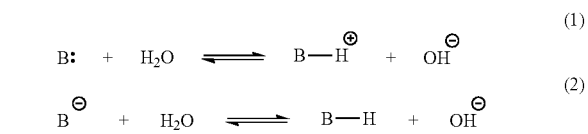

The term "hydrogel matrix" as used herein refers to a compound of the disclosure which has been dissolved in water or an aqueous solution and forms a gel or matrix comprised of strong intermolecular hydrogen bonding and/or ionic bonding between the weakly basic polymers and BHB, where the matrix can absorb additional ketogenic precursors. When ketogenic precursors are incorporated into the matrix their repulsive taste is suppressed.

The term "ingestible" as used herein refers to a weakly basic polymer which may be administered to a subject, such as a human, with few, or negligible, side effects.

The term "non-digestible" as used herein refers to a weakly basic polymer which is mostly, or fully, resistant to digestion by the secretions of a subject's gastrointestinal tract, and is excreted from the body.

The term β-hydroxybutyric acid (BHB) as used herein refers to a compound having the structure

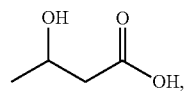

and includes all stereoisomers thereof.

Compositions of the Disclosure

The present disclosure relates to ingestible and palatable ketogenic compounds of β-hydroxybutyric acid and a weakly basic polymer. In one embodiment, the weakly basic polymer is comprised of monomers comprising weak-base functional groups, and the molar ratio between each weak-base functional group and the BHB is about 1:1. In further embodiments, the compound comprising β-hydroxybutyric acid and the weakly basic polymer (at the about 1:1 ratio) forms a hydrogel-matrix when dissolved in water which traps the BHB within the matrix such that the repulsive taste of the BHB is suppressed when the compound is administered orally. In further embodiments, the hydrogel-matrix is able to absorb and/or incorporate additional ketogenic precursors, such as additional BHB, including dimers, trimers, tetramers and oligomers of BHB, polymers of BHB, 1,3-butanediol and/or acetoacetic acid or esters thereof, and wherein the matrix maintains taste neutralization of the BHB and/or other precursors. In further embodiments, upon ingestion, the compounds of the disclosure release the BHB which are absorbed and elevate ketogenesis in a subject, while the weakly basic polymers are not absorbed by the system and are excreted.

In one embodiment of the disclosure, there is included compounds comprising:
(i) 3-hydroxybutyric acid (β-hydroxybutyric acid); and
(ii) a weakly basic polymer comprising weak base functional groups.

In one embodiment, the weakly basic polymer comprises weak-base functional groups, and the molar ratio between the weak-base functional groups and the BHB in the compound is about 1:1. In some embodiments, the compounds comprising BHB and the weakly basic polymer are weak-acid weak-base salt compounds (ionic compounds) or weak-acid weak-base buffered salt compounds.

In a further embodiment, the present disclosure also includes a hydrogel comprising:
(i) β-hydroxybutyric acid (BHB); and
(ii) a weakly basic polymer comprising weak-base functional groups;
wherein the molar ratio of the BHB to the weak-base functional groups is at least about 1:2, and suitable to form a hydrogel matrix.

In further embodiments, in the hydrogel matrix, the BHB is trapped within a matrix of strong intermolecular interactions, which upon administration to a subject, is used as an alternative energy substrate or elevates blood concentrations of ketone bodies. In some embodiments, elevation of ketone bodies leads to the enhancement of physical and cognitive performance and to the prevention, amelioration or treatment of a medical condition in which ketosis is involved. In one embodiment, upon administration of the complexes to a subject, the concentration of ketones in the blood stream is increased.

In one embodiment, the compounds of the disclosure allows a subject to ingest significant amounts of BHB with minimal or no mineral load, as the accompanying weakly basic polymer is excreted upon the release of BHB in the bloodstream and tissues.

In one embodiment, the weakly basic polymer comprises weak-base functional groups, and the molar ratio between each weak-base functional group of the polymer and the BHB is about 1:1. In further embodiments, BHB is hydrogen-bonded to a weak-base functional group of the weakly basic polymer. In some embodiments, the compounds comprising BHB and the weakly basic polymer are weak-acid weak-base salt compounds (ionic compounds) or weak-acid weak-base buffered salt compounds. A weak base buffered salt is defined as a salt composition where a weak acid, and a weak base and their conjugate acid and conjugate base pairs are present. In a further embodiment, in a composition where the molar ratio of BHB is greater than the weak base monomer, the composition implicitly contains the 1:1 compound as described, the extra BHB being H-bonded to the compound (e.g. 2:1), or when the BHB is less, the extra weak base monomer remains in its free form or is unreacted.

In one embodiment, the BHB is a racemic mixture of D and L; or a mixture where the D isomer is enriched (i.e, >50%) or a pure D-BHB isoform.

In further embodiments, the compound of β-hydroxybutyric acid and a weakly basic polymer forms a hydrogel matrix when dissolved in water, and can absorb further ketogenic precursors. In one embodiment, the present disclosure includes a composition comprising the hydrogel matrix of β-hydroxybutyric acid and a weakly basic polymer in water, and additional ketogenic precursors, such as additional BHB, wherein the taste of the additional BHB is also neutralized as a result of it being trapped within the hydrogel matrix. In one embodiment, the hydrogel matrix absorbs additional BHB such that BHB is present in the hydrogel matrix in a molar ratio of great than about 1:1, or greater than about 2:1 (BHB:weak-base functional groups), or greater than 5:1, or about 10:1. In other embodiments, the hydrogel matrix can absorb other ketogenic precursors such as poly-β-hydroxybutyric, wherein the poly-β-hydroxybutyric (polyBHB) is a dimer, trimer, tetramer or an oligomer (or other hydrolyzed products of poly-BHB) wherein the number of BHB residues in the oligomer is between about 5 and about 20 as a short-chain oligomer, and between about 21 to about 50 for a medium-chain oligomer. In further embodiments, the polyBHB is a long chain polymer having more than 50 BHB residues. In another embodiment, the ketogenic precursors included in the composition are 1,3-butanediol, or acetoacetic acid.

In one embodiment, the compound of the disclosure has the formula $[(\text{weakly basic polymer})^+(\text{BHB})^-]_x$, wherein the variable "x" can range from between about 2 to about 1000, and the weakly basic polymer comprises weak base functional groups. In one embodiment, the BHB and the weak base functional groups of the weakly basic polymer are present in a ratio of about 1:1 to about 1:2 (BHB:weak base functional groups).

In one embodiment, the weakly basic polymer is an ingestible polymer. In another embodiment, the weakly basic polymer is non-digestible. In one embodiment, the weakly basic polymer is a polysaccharide.

In some embodiments, the weakly basic polymer is comprised of weakly basic monomer units (having weak base functional groups) having a pKb of between about 4.0 to 10.5. In another embodiment, the weakly basic polymer is a copolymer which is further comprised of monomers which do not have weakly basic moieties.

In one embodiment, the weakly basic polymer is chitosan, carboxymethylcellulose, carboxymethylchitosan, alginates, proteins and polypeptides, such as polylysine, and other polysaccharides containing carboxylic acid and/or carboxylate groups, such as glucuronic acid, mixtures thereof or derivatives thereof. In one embodiment, the weakly basic polymer is chitosan having glucosamine residues which have a pKb of about 6.42. In another embodiment, the weakly basic polymer is carboxymethylcellulose having carboxymethyl residues which have a pKb of about 9.70. In one embodiment, the weakly basic polymer is sodium carboxymethylcellulose.

In one embodiment, the weakly basic monomer units comprise weak base functional groups such as carboxymethyl groups, carboxylic acid groups, carboxylate groups, amine groups, phosphate groups or derivatives thereof (such as phosphoramides), or sulfates and sulfites.

In one embodiment, chitosan has the formula $[(\text{glucNH}_2)_n (\text{glucNHAc})_m]$, wherein $(\text{glucNH}_2)$ is a glucosamine residue, and (glucNHAc) is an N acetylglucosamine residues. In further embodiments, the variable "m" may vary from 0% to about 30% of the total residues n+m (and n being about 70% to about 100%). In some embodiments, the number of residues n+m, may vary from dimer, n+m=2; trimer, n+m=3; oligomers where n+m ranges from 4 to 50 and higher polymers where n+m corresponds to a mass range of 9 kD to 300 kD. In some embodiments, n+m is an integer from 2 to about 1000.

In some embodiments, carboxymethylcellulose (CMC) has the formula $\{[\text{glu}(\text{CH}_2\text{CO}_2)_x\text{M}_x]_n(\text{glu})_m]\}$ wherein [glu$(\text{CH}_2\text{CO}_2)_x\text{M}_x$] are carboxymethyl glucose residues, and where the degree of carboxymethylation, x=1 or 2 or 3 and M can be cations with charge, +1 or +2 or +3. In another embodiment, the glucose residues (glu), m vary from 30% to 0% of the total residues n+m (and n being about 70% to about 100%). In some embodiment, the number of residues, n+m may vary from dimer, n+m=2; trimer, n+m=3; oligomers where n+m ranges from 4 to 50 and higher polymers where n+m corresponds to a mass range of 9 kD to 300 kD. In some embodiments, n+m is an integer from 2 to about 1000.

In one embodiment, the compound of the present disclosure has the following structure when the weakly basic polymer is chitosan as shown in Scheme 1.

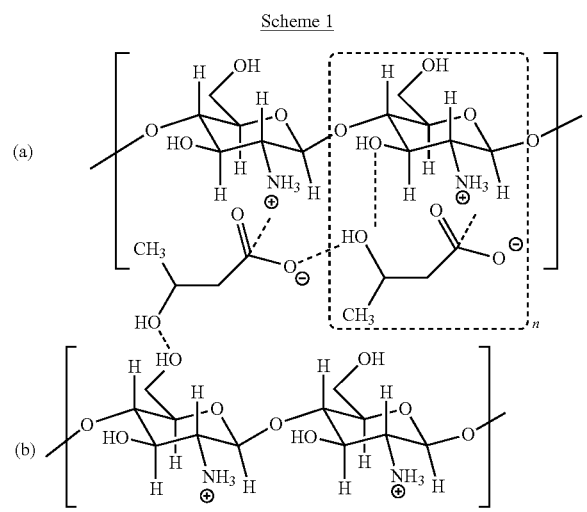

Scheme 1

In one embodiment, and referring to Scheme 1, which shows two of numerous possible H-bonding and ionic interactions in the matrix of a chitosan-BHB compound, in a molar ratio of 1:1 (BHB:weak base functional group ($NH_2$)). Scheme 1 shows a compound derived from chitosan, $[(glucNH_2)_n(glucNHAc)_m]$, where m=0, and is represented by the formula $[(glucNH_3^+)(BHB^-)]_x$, where "x" can range from about 2 to about 1000. Scheme 1 shows the basic repeating unit of chitosan-BHB, and in (a) shows adjacent BHB residues interacting via ionic and H-bonding interaction leading to a non-covalent BHB structure, while (b) shows BHB interactions with adjacent chitosan chains leading to the matrix structure of the complex.

In another embodiment, the complex of the present disclosure has the following structure when the weakly basic polymer is CMC as shown in Scheme 2.

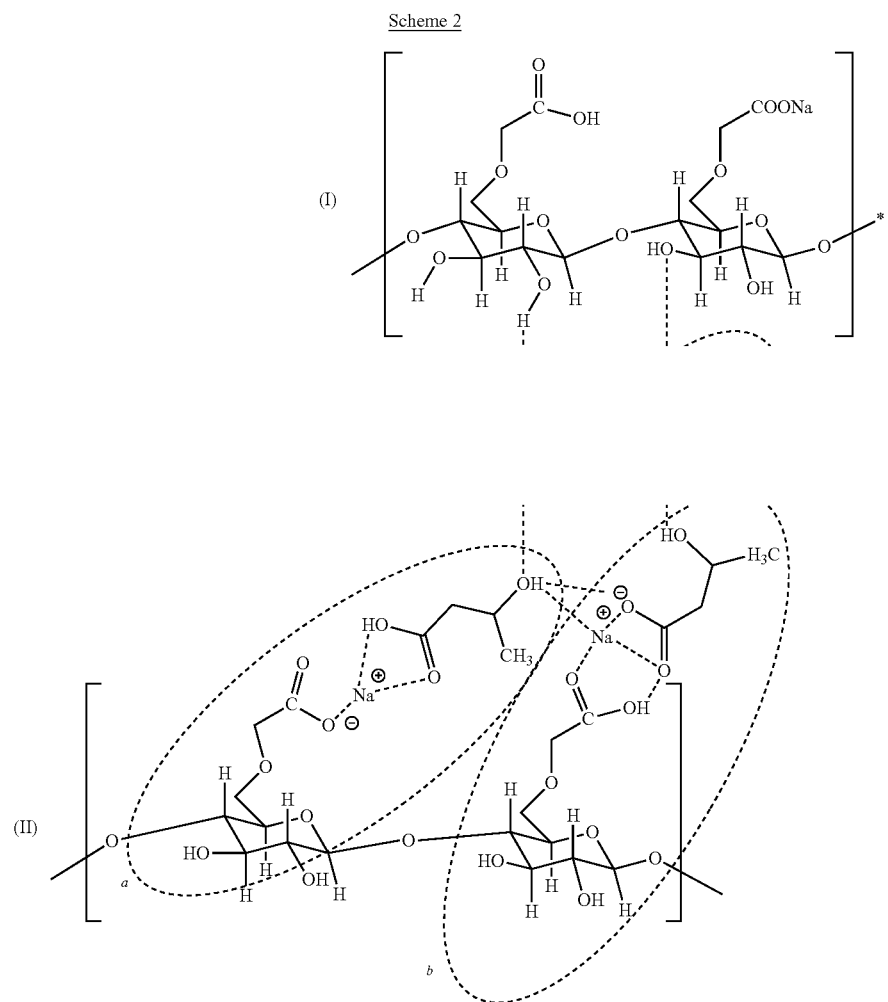

Scheme 2

In one embodiment, and referring to Scheme 2, which shows two of numerous possible H-bonding and ionic interactions in the matrix of the complex of a CMC-BHB compound, in a molar ratio of 1:1 (BHB:weak base functional group). Scheme 2 shows a compound derived from CMC, $[(glu(CH_2CO_2)_xM]_x)_n(glu)_m]$, where m=0, and x=1, and is represented by the formula $\{(glu(CH_2CO_2M)(BHB)]_a [(glu(CH_2CO_2H)(BHBM)]_b\}$, where "a+b" can range from about 2 to about 1000. In one embodiment, M is a mineral ion, such as sodium. Within the oval rings of Scheme 2 is shown the basic repeating unit of CMC-BHB, and in (I) shows adjacent BHB residues interacting via ionic and H-bonding interaction leading to a non-covalent poly-BHB structure, while (II) shows BHB interactions with adjacent CMC chains leading to the matrix structure of the complex.

In another embodiment, Scheme 3 shows the variations in the weakly basic polymers chitosan and carboxymethylcellulose.

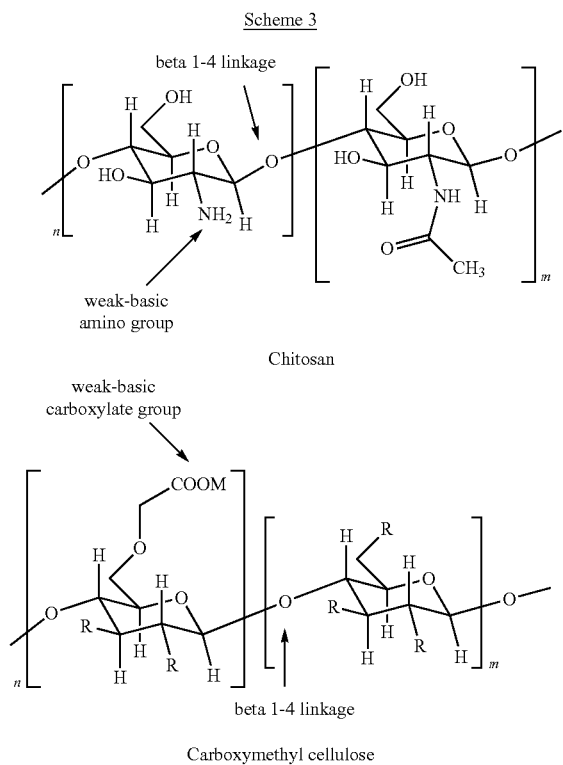

In one embodiment, weakly basic polymers, such as chitosan and CMC, form strong hydrogen bonds and ionic interactions due to hydroxyl groups and weak base functional groups. In one embodiment, the structure of the complex shows the hydroxyl groups and weak-base functional groups from the polymer backbone interacting with multiple BHB molecules. In one embodiment, the interactions between the polymer and BHB are strong intermolecular hydrogen bonding and ionic bonding. In one embodiment, the organization of hydroxyl and weak-base functional groups act as a template and in turn organize the BHB into a non-covalent polymer like assembly.

In further embodiments, the non-covalent polymeric complex is supported by a network of intermolecular hydrogen and ionic bonding; the carboxyl and the beta-hydroxyl groups of BHB, and the many hydroxyl and weak base groups of the polymer back bone. In one embodiment therefore, the complex is a matrix of hydrogen bonding and ionic bonding organized by the polymer template.

In further embodiments, the complex has weak acid and weak base functional groups and therefore is a polymeric buffer. In one embodiment, this polymeric buffer is like a very concentrated buffer of monomeric weak acid weak base mixture. The buffering property combined with matrix structure of the compound manifest characteristics that are favorable in the application as a ketone supplement. In one embodiment, the buffering capacity of the compound, when mixed with up to five-fold BHB can give a palatable formulation with a pH range of between about 3.0 to about 8.0, for example 4.5±1.0.

In other embodiments of the disclosure, an acidic nutrient can be incorporated into the weakly basic polymer, when the weakly basic polymer has, for example, nitrogen residues, such as chitosan, by reacting a percent fraction of the basic residues, in chitosan (glucNH$_2$) to form a glucosammonium salt. In one embodiment, the glucosammonium residues carrying the nutrient (A) can be represented as (glucNH$_3^+$)$_d$ A) where A can have charges −1 or −2 or −3 and d can be 1, 2, 3. In one embodiment, the nutrient A is the anion of acidic molecules such as amino acids, fatty acids and combinations thereof or nutrient molecules that bear a carboxylate, sulfate, sulfo or a phosphate or derives of these groups. In one embodiment, the percent transformation of glucosamine (glucNH$_2$) to (glucNH$_3^+$)$_d$A) may vary from 50% to 0%.

In other embodiments, when the weakly basic polymer has carboxylate residues (or other anionic residues), exchanging a percent fraction of the mineral cation, M in some residues of carboxymethyl glucose residues, [glu (CH$_2$CO$_2$)$_x$M$_x$] where M=Na$^+$ with other mineral nutrients or organic nutrient cations, incorporates these nutrients into CMC polymer. In some embodiments, the carboxymethyl residues can be represented as (glu(CH$_2$CO$_2$)$_x$B) where x=to the charge of the nutrient cation and B is a nutrient cation with charges +1 or +2 or +3 or 4+ and x can be 1, 2, 3, 4. In one embodiment, nutrient B is (i) mineral ions of K, Na, Ca, Mg etc, (ii) micronutrient ions like Fe, Cr, Mn, etc and (iii) organic based nutrient cations such as amino acids, etc or nutrients that contain a nitrogen base. In one embodiment, the percent transformation of [glu(CH$_2$CO$_2$)$_x$M$_x$] to [glu (CH$_2$CO$_2$)$_x$B] ranges from about 50% to 0%.

In one embodiment of the disclosure, the compounds of the disclosure possess a sour or citrus taste, whereas pure BHB solutions are nauseating and the weakly basic polymers have slightly bitter tastes (consistent with their basic structure). In one embodiment, the compounds of the disclosure have improved palatability of compositions containing BHB.

In one embodiment of the disclosure, the compounds form weak-acid weak-base salts, as the weakly basic polymers react in an acid/base reaction with β-hydroxybutyric acid. In one embodiment, when the weakly basic polymer is carboxymethylcellulose, the polymer has both carboxylic (—COOH) and carboxylate (COO$^-$) groups where the carboxylate groups react with BHB acid to for weak acid weak base buffered salt where the acids and the corresponding conjugate bases both the CMC and BHB are present. In another embodiment, when the weakly basic polymer is chitosan, the amine groups function as the basic functionality to react with the BHB-acid to form a weak-acid weak-base salt.

In one embodiment, the compounds of the disclosure are stable matrices which retain the BHB within the polymeric matrix and prevent the BHB from escaping from the matrix. Accordingly, in one embodiment, the stable complexes retain their improved palatability when formulated as compositions for food products etc.

In one embodiment, the concentration of the BHB as a result of the dissolution of the compound and/or hydrogel in water or aqueous solution which maintains taste suppression of the BHB is at least about 1.0%, at least about 2.0%, at least about 3.0%, at least about 5.0%, at least about 6.0%, at least about 7.0%, at least about 10.0%, at least about 15.0%, at least about 20.0%, at least about 25.0%, at least about 30.0%, at least about 40.0%, at least about 50.0%, at least about 60.0%, at least about 70.0% (weight/volume). In one embodiment, the concentration of the BHB as a result of the dissolution of the compound and/or hydrogel in water or aqueous solution which maintains taste suppression of the BHB is about 1.0%-70.0%, about 1.0%-60.0%, about 1.0-50.0%, about 1.0%-40.0%, about 2.0%-30.0%, about 3.0%-20.0%, about 5.0%-10.0%, (weight/volume). In other embodiments, the concentration of the BHB as a result of the dissolution of the compound and/or hydrogel in water or aqueous solution which maintains taste suppression of the BHB is at least about 0.10 mol/L, at least about 0.20 mol/L, at least about 0.30 mol/L, at least about 0.40 mol/L, at least about 0.50 mol/L, at least about 0.60 mol/L, at least about 0.70 mol/L, at least about 0.80 mol/L, at least about 0.90 mol/L, at least about 1.00 mol/L, at least about 1.50 mol/L, at least about 2.00 mol/L, at least about 3.00 mol/L, or at least about 5.00 mol/L. In other embodiments, the concentration of the BHB as a result of the dissolution of the compound and/or hydrogel in water or aqueous solution which maintains taste suppression of the BHB is about 0.10-5.00 mol/L, about 0.10-3.00 mol/L, about 0.10-2.00 mol/L, about 0.10-1.00 mol/L, or about 0.30-0.80 mol/L. In a further embodiment, the weakly basic polymer, such as CMC or chitosan, is present at a concentration within the compound in an aqueous solution of at least about 0.10%, at least about 0.5%, at least about 1.0%, at least about 2.0%, at least about 3.0%, at least about 4.0%, at least about 5.0%, at least about 10.0%, at least about 20.0%, or at least about 25.0%, (weight/volume). In a further embodiment, the weakly basic polymer, such as CMC or chitosan, is present at a concentration within the compound in an aqueous solution of about 0.10-25.0%, about 0.1%-10.0%, about 0.1-5.0%, or about 1.0-5.0% (weight/volume).

In other embodiments, the compound is present in a solid form and useful in solid forms of administration such as a chocolate bar, baked good, candy, and the concentration of BHB with maintenance of taste suppression is at least about 1.0%, at least about 2.0%, at least about 3.0%, at least about 5.0%, at least about 10.0%, at least about 15.0%, at least about 20.0%, at least about 25.0%, at least about 30.0%, at least about 40.0%, at least about 50.0%, at least about 60.0%, at least about 70.0%, at least about 80.0% (weight/weight). In further embodiments, the compound is present in a solid form and useful in solid forms of administration such as a chocolate bar, baked good, candy, and the concentration of BHB with maintenance of taste suppression is about 1.0-80.0%, about 1.0-50.0%, about 5.0-50%, about 10.0-40.0%, or about 20.0-30.0% (weight/weight). In a further embodiment, the weakly basic polymer, such as CMC or chitosan, is present at a concentration within the solid compound of at least about 1.0%, at least about 2.0%, at least about 3.0%, at least about 4.0%, at least about 5.0%, at least about 5.0%, at least about 6.0%, at least about 7.0%, at least about 10.0%, at least about 20.0%, or at least about 25.0%, (weight/weight). In a further embodiment, the weakly basic polymer, such as CMC or chitosan, is present at a concentration within the solid compound of about 1.0-25.0%, about 1.0-10.0%, or about 5.0-10.0% (weight/weight).

The present disclosure also includes a method for masking the taste of BHB which is associated with a bitter taste, which includes the steps of: providing a weakly basic polymer, and mixing the polymer in an aqueous solution such as water, for example at a temperature of between 15-50° C. and obtaining a uniform suspension. In a further embodiment, the suspension is stirred to obtain a clear solution. BHB is dissolved in water and slowly added to the weakly basic polymer suspension, and with optional stirring, the solution is maintained at a temperature of between 15-50° C., such as 35° C. A viscous liquid is obtained and kept at room temperature, for example for about 1-4 hours, and the liquid is dried to obtain the compound as a matrix.

In other embodiments, the compound of the present disclosure is obtained by dissolving BHB in water, for example at a temperature of about 15-50° C., such as 25° C., and slowly adding a weakly basic polymer under vigorous stirring to obtain a thick liquid. Upon stirring for an additional 1-4 hours, to obtain a thick liquid, which is then dried to obtain the compound as a matrix.

In another embodiment, the present disclosure comprises a composition comprising BHB, and a weakly basic polymer, to obtain a matrix, wherein the composition is substantially free of the repugnant taste of BHB.

Methods of Medical Treatment and Uses of the Compounds and/or Hydrogel

In one embodiment of the disclosure, the compounds and/or hydrogels of the present disclosure are useful to increase ketone levels in the bloodstream when administered a subject. In further embodiments, the compounds or hydrogels are formulated for the preparation of a food product, a beverage, a drink, a food supplement, a dietary supplement, a functional food, a nutraceutical or a medicament.

In other embodiments, the compounds and/or hydrogels are formulated for the preparation of a food product, a beverage, a drink, a food supplement, a dietary supplement, a functional food, a nutraceutical or a medicament for promoting ketosis in a mammal.

In other embodiments, the compounds and/or hydrogels are formulated for the preparation of a food product, a beverage, a drink, a food supplement, a dietary supplement, a functional food, a nutraceutical or a medicament for promoting weight loss or suppressing appetite in a mammal.

In other embodiments, the compounds and/or hydrogels are formulated for the preparation of a food product, a beverage, a drink, a food supplement, a dietary supplement, a functional food, a nutraceutical or a medicament for preventing or treating neurodegenerative conditions in a mammal.

In other embodiments, the compounds and/or hydrogels are formulated for the preparation of a food product, a beverage, a drink, a food supplement, a dietary supplement, a functional food, a nutraceutical or a medicament for preventing or treating traumatic brain injuries in a mammal.

In other embodiments, the compounds and/or hydrogels are formulated for the preparation of a food product, a beverage, a drink, a food supplement, a dietary supplement, a functional food, a nutraceutical or a medicament for treating a condition caused by muscle impairment or muscle fatigue.

In other embodiments, the compounds and/or hydrogels are formulated for the preparation of a food product, a beverage, a drink, a food supplement, a dietary supplement, a functional food, a nutraceutical or a medicament for the prevention or the improvement of treatment for cancer.

In other embodiments, the compounds and/or hydrogels are formulated for the preparation of a food product, a beverage, a drink, a food supplement, a dietary supplement, a functional food, a nutraceutical or a medicament to regulate or lower blood glucose levels.

In other embodiments, the compounds and/or hydrogels are formulated for the preparation of animal feed product or additives in the farming of animals to improve the quality and production of milk in milk producing animals, improve the quality and production of eggs in birds and improve the quality and production of meat in meat producing animals.

In further embodiments, the compounds and/or hydrogels of the disclosure elevate and sustain blood ketone levels through the administration of therapeutically effective amounts of the compounds and results in a rapid and sustained elevation of blood ketones upon, for example, oral administration. In some embodiments, between about 1 gram to about 50 g of BHB is administered to a subject when administered as part of the compounds and/or hydrogels of the disclosure. In further embodiments, administration of the complexes results in a rapid and sustained state of ketosis for the patient or subject.

In one embodiment, the compounds and/or hydrogels of the disclosure are useful for treating fetal alcohol syndrome disorder.

In some embodiments, the compounds and/or hydrogels are useful for weight loss or treatment of high blood glucose or type II diabetes. In further embodiments, the compounds or hydrogels are used for weight loss, to enhance cognitive ability or brain function, to enhance athletic performance and to improve overall metabolic health.

In other embodiments, the induced ketosis as a result of administration of the compounds can suppress appetite, induce weight loss, increase athletic endurance, control blood sugar concentrations and be used to treat epilepsy, and/or diabetes.

In some embodiments, the compounds and/or hydrogels are administered, for example, orally, for example as a drink, once a day, twice a day, three times a day or more.

In further embodiments, the compounds and/or hydrogels are formulated as tablet, capsules, powdered mixtures, or ready to drink liquids, or any other formulation well known in the art.

In some embodiments, the compounds and/or hydrogels are administered to patients or subjects, and a patient means any member of the animal kingdom, including humans, gorillas, monkeys, rodents, etc.

The present disclosure also includes a method for inducing ketosis in a subject comprising administering to the subject a therapeutically effective amount of a compound and/or hydrogel of the disclosure, wherein the compound and/or hydrogel maintains taste suppression of the BHB. In another embodiment, the compound and/or hydrogel is administered at an amount (as part of the compound and/or hydrogel) to provide an effective BHB concentration of at least about 1.0%, at least about 2.0%, at least about 3.0%, at least about 5.0%, at least about 6.0%, at least about 7.0%, at least about 10.0%, at least about 15.0%, at least about 20.0%, at least about 25.0%, at least about 30.0%, at least about 40.0%, at least about 50.0%, at least about 60.0%, at least about 70.0% (weight/volume), and still maintain taste suppression. In other embodiments, the compound and/or hydrogel is administered at an amount (as part of the compound and/or hydrogel) to provide an effective BHB concentration of at least about 1 g/L, at least about 2 g/L, at least about 5 g/L, at least about 10 g/L, at least about 15 g/L, at least about 20 g/L, at least about 30 g/L, at least about 50 g/L, at least about 100 g/L, at least about 200 g/L, or at least about 400 g/L.

In one embodiment, the compounds of the disclosure can be administered as isolated compounds or solutions (hydrogels), or the compounds can be administered as a part of a formulation.

The compounds can be formulated in a composition for administration to a subject as an edible solid, such as a chocolate bar, gummy, baked good, or as a beverage containing the compound and/or hydrogel, or as an oral solid, semi-solid, or liquid pharmaceutical composition, such as a tablet (e.g., flash, chewable, buccal, sublingual, effervescent, or simply swallowed), capsule (hard-shelled or soft-shelled), pill, granules, powder (bulk powder or divided powder), oral suspension, syrup, elixir, oral drops, emulsion (oil-in-water or water-in-oil), pastilles, lozenge.

The compounds and compositions containing them can be formulated according to known methods for preparing pharmaceutically useful compositions. Formulations are described in a number of sources which are well known and readily available to those skilled in the art. For example, Remington's Pharmaceutical Science (Martin 1995) describes formulations which can be used in connection with the compounds. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents.

In certain embodiments, the compounds and/or composition described herein may also include one or more nutritional substrates such as free amino acids, amino acid metabolites, vitamins, minerals, electrolytes and metabolic optimizers such as NADH, soluble ubiquinol, tetrahydrobiopeterin, α-ketoglutaric acid, carnitine, and/or a lipoic acid, nutritional co-factors, calcium β-methyl-β-hydroxybutyrate, arginine α-ketoglutarate, sodium R-α lipoic acid, thiamine, riboflavin, niacin, pyridoxine, ascorbic acid, citric acid, malic acid, sodium benzoate, potassium sorbate, acesulfame K, aspartame, xanthan gum, or a combination thereof. Nonlimiting examples of nutritional co-factors include R-α lipoic acid, acetyl-1-carnitine, ketoisocaproate, α-ketoglutarate, α-hydroxyisocaproate, creatine, branched chain amino acids (leucine, isoleucine, valine), β-hydroxy-β-methylbutyrate (FMB), B vitamins, vitamin C, soluble ubiquinol, and carnitine to assist in mitochondrial function. In certain embodiments, the composition is dosed to provide no more than 400 calories per day Although the disclosure has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

EXAMPLES

The operation of the disclosure is illustrated by the following representative examples. As is apparent to those skilled in the art, many of the details of the examples may be changed while still practicing the disclosure described herein.

Example 1—Synthesis of Carboxymethyl-BHB

The degree of carboxymethylation of glucose was taken as one and therefore the molecular weight of monomers as 242.2 g/mol. Sodium-CMC (1.38 g, 5.7 mmol) powder was added to a rapidly stirred warm water (35° C., 45 mL) contained in a round bottom flask (150 mL), yielded an uniform suspension. Stirring the suspension for a period of 45 to 60 min gave a clear solution. BHB (0.62 g, 6.0 mmol) was dissolved in water (5 mL) and this solution was added slowly (span of 15 min) to the sodium-CMC solution kept at 35 C. The reaction mixture became very viscous within a few minutes and was kept at room temperature for 4 hours. The flask was attached to vacuum manifold and was dried under dynamic vacuum until there was no further reduction of the total mass of the reaction mixture (12 to 16 h, 1 mT). The drying process forces the formation of the matrix and the compound had a glassy semisolid appearance.

Example 2—Synthesis of Chitosan-BHB

Commercial chitosan upon suspension in water gave a pH in the range of 4 to 6, suggesting the presence of a substantial quantity of glucosammonium residues. The chitosan was suspended in NaOH (10 g chitosan/100 mL, 0.1 M NaOH) and was stirred overnight at 25 C. The suspension was filtered through a medium porosity frit and the chitosan was washed repeatedly with water until the pH of the eluent was neutral. The molecular weight of chitosan monomers was taken as 161.2 g/mol.

BHB (0.227 g, 2.2 mmol) was dissolved water (25 mL) contained in a round bottom flask (100 mL). The flask was immersed in a water bath (25 C) and Chitosan (0.371 g, 2.3 mmol) powder was added slowly (span of 20 min) under vigorous stirring. The reaction is slightly exothermic, and the mixture became very thick. Upon stirring (1 to 1.5 h) a clear colourless to faintly yellowish thick liquid was obtained. The flask was attached to vacuum manifold and was dried under dynamic vacuum until there was no further reduction of the total mass of the reaction mixture (12 to 16 h, 1 mT). The drying process forces the formation of the matrix and the compound had a glassy semisolid appearance.

Example 3—pH of the Compounds

The pH of pure BHB varies between 2.3 and 2.6 and has a pKa of about 4.4. However, mixing pure BHB with the weakly basic polymers to form the compounds in excess of 1:6 mole ratios (polymer:BHB), resulted in solutions having pHs in the range 4+/−0.5, which is consistent with the buffering effect of a weak-acid/weak-base salt.

Example 4—Taste of the Compounds

The formulation of BHB with the weakly basic polymers has shown significant improvement in palatability over free BHB. A total of 11 individuals ages ranging from 21 to 70 tasted the formulation with BHB:weak base (molar ratio 5:1) at least 3 times. The formulation comprised a composition totaling 5 grams BHB diluted in 75 ml of water. Participants were asked to score the taste of the formulation on a scale from 1 to 10. For the BHB-Chitosan, participants scored an average of 7.3/10 and for CMC-BHB, 9.2/10. All individuals had previously tested a formulation comprising 5 grams of free BHB diluted in 75 ml of water. Participants unanimously scored an average 0/10 for the free BHB formulation and participants could not drink even small amounts of the 75 ml portion. Aside from the repulsive (or intolerable) taste, participants complained that the harshness of the plain BHB remained present hours after ingestion.

Discussion

The improvement in taste of the compounds of the disclosure containing BHB indicates that the matrix structure of the hydrogels is playing a role in masking the intolerable taste of the BHB, Without being bound by theory, it is believed that the matrix of the compounds incorporates BHB molecules by expanding the flexible hydrogen bonding network, shielding the BHB from the taste receptors in the oral cavity. In the formulations of the present disclosure, even though the amount of BHB is high, the taste of the polymeric complexes was pleasant, indicating a low, or negligible, amount of free BHB which escapes from the matrix.

Example 5—Administration of Compounds

To determine the time course of ketosis, the tested subjects were orally given the test substances of a BHB-CMC complex diluted in distilled water. Blood concentrations of glucose and BHB were determined utilizing a commercially available glucose/ketone monitoring system (Abbott FreeStyle Precision Neo® blood glucose and ketone meter) at defined time points (0, 15, 30, 80, 120 and 240 minutes following ingestion of the test substances).

Table 1 shows blood BHB levels (mmol/L) of a 75 kg healthy male subject following a single daily oral administration of BHB-CMC compound comprised of 10 grams BHB and 2 grams CMC diluted in 150 mL of distilled water at 15, 30, 60, 120 and 240 minutes on two consecutive days.

Table 2 shows blood BHB levels (mmol/L) of a 85 kg diabetic male (Type-2 on short and long acting insulin) subject following a single daily oral administration of BHB-CMC compound comprised of 5 grams BHB and 1 gram CMC diluted in 75 mL of distilled water at 15, 30, 60, 120 and 240 minutes on two consecutive days.

As clearly seen in the Tables, administration of complexes of the disclosure resulted in increased levels of BHB in the blood of the tested subjects.

While the present disclosure has been described with reference to what are presently considered to be the preferred examples, it is to be understood that the application is not limited to the examples described herein. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

TABLE 1

Blood BHB Levels (mmol/L) in Healthy Male

| Time min | Day 1 mmol/L | Day 2 mmol/L | Mean mmol/L |
| --- | --- | --- | --- |
| 0 | 0.2 | 0.1 | 0.15 |
| 15 | 0.6 | 0.5 | 0.55 |
| 30 | 0.8 | 0.7 | 0.75 |
| 60 | 1.1 | 1.0 | 1.05 |

TABLE 1-continued

Blood BHB Levels (mmol/L) in Healthy Male

| Time min | Day 1 mmol/L | Day 2 mmol/L | Mean mmol/L |
|---|---|---|---|
| 120 | 1.0 | 0.9 | 0.95 |
| 180 | 0.4 | 0.3 | 0.35 |

TABLE 2

Blood BHB Levels (mmol/L) in Diabetic Male

| Time min | Day 1 mmol/L | Day 2 mmol/L | Mean mmol/L |
|---|---|---|---|
| 0 | 0.2 | 0.2 | 0.20 |
| 15 | 0.5 | 0.5 | 0.50 |
| 30 | 0.7 | 0.5 | 0.60 |
| 60 | 0.8 | 0.6 | 0.70 |
| 120 | 0.7 | 0.5 | 0.60 |
| 180 | 0.3 | 0.3 | 0.30 |

REFERENCES

Patents

U.S. Pat. No. 6,323,237
U.S. Pat. No. 8,642,654
U.S. Pat. No. 9,138,420
United States Patent Publication no. 2003/0022937
United States Patent Publication no. 2010/0041751

Journal Articles

Kashiwaya Y, Takeshima T, Mori N, Nakashima K, Clarke K, Veech R L. (2000). D-beta-hydroxybutyrate protects neurons in models of Alzheimer's and Parkinson's disease. Proc Natl Acad Sci USA, 97(10):5440-4.

Veech R L. (2013) Ketone esters increase brown fat in mice and overcome insulin resistance in other tissues in the rat. Ann N Y Acad Sci, 1302, 42-48.

Veech, R L. (2014) Ketone ester effects on metabolism and transcription. J Lipid Res, 55(10), 2004-2006.

Arakawa, T., Goto, T., & Okada, Y. (1991). Effect of ketone body (d-3-hydroxybutyrate) on neural activity and energy metabolism in hippocampal slices of the adult guinea pig. Neuroscience Letters, 130(1), 53-56.

Hertz, L., Chen, Y., & Waagepetersen, H. S. (2015). Effects of ketone bodies in Alzheimer's disease in relation to neural hypometabolism, β-amyloid toxicity, and astrocyte function. Journal of Neurochemistry, 134(1), 7-20.

Youm, Y.-H., Nguyen, K. Y., Grant, R. W., Goldberg, E. L., Bodogai, M., Kim, D., Dixit, V. D. (2015). The ketone metabolite β-hydroxybutyrate blocks NLRP3 inflammasome-mediated inflammatory disease. Nature Medicine, 21(3), 263-269.

Kumar Dutta, P., Dutta, J., & Tripathi, V. S. (2004). Chitin and chitosan: Chemistry, properties and applications. Journal of Scientific & Industrial Research, 63 (January), 20-31.

Samoilova, M., Weisspapir, M., Abdelmalik, P., Velumian, A. A., & Carlen, P. L. (2010). Chronic in vitro ketosis is neuroprotective but not anti-convulsant. Journal of Neurochemistry, 113(4), 826-835.

Newman, J. C., & Verdin, E. (2014). Ketone bodies as signaling metabolites. Trends in Endocrinology and Metabolism, 25(1), 42-52.

Wensvoort, J., Kyle, D. J., Orskov, E. R., & Bourke, D. A. (2001). Biochemical adaptation of camelids during periods where feed is withheld. Rangifer, 21(1), 45-48.

White, H., & Venkatesh, B. (2011). Clinical review: Ketones and brain injury. Critical Care, 15(219), 1-10.

Cox, P. J., & Clarke, K. (2014). Acute nutritional ketosis: implications for exercise performance and metabolism. Extreme Physiology & Medicine, 3(1), 17.

Poff, A. M., Ari, C., Arnold, P., Seyfried, T. N., & D'Agostino, D. P. (2014). Ketone supplementation decreases tumor cell viability and prolongs survival of mice with metastatic cancer. International Journal of Cancer, 135(7), 1711-1720.

Prins, M. L. (2008). Cerebral Metabolic Adaptation and Ketone Metabolism after Brain Injury. Journal of Cerebral Blood Flow & Metabolism, 28(1), 1-16.

Lincoln, B. C., Rosiers, C. Des, & Brunengraber, H. (1987). Metabolism of S-3-hydroxybutyrate in the perfused rat liver. Archives of Biochemistry and Biophysics, 259(1), 149-156.

Murphy, J. J., Bastida, D., Paria, S., Fagnoni, M., & Melchiorre, P. (2016). Asymmetric catalytic formation of quaternary carbons by iminium ion trapping of radicals. Nature, 532(7598), 218-222.

Gasior, M., Rogawski, M. A., & Hartman, A. L. (2006). Neuroprotective and disease-modifying effects of the ketogenic diet. Behavioural Pharmacology, 17(5-6), 431-9.

Sena, S. F. (2010). Beta-hydroxybutyrate: New Test for Ketoacidosis. Department of Pathology and Laboratory Medicine, 4(8), 1-2.

Yamada, T., Zhang, S.-J., Westerblad, H., & Katz, A. (2010). {beta}-Hydroxybutyrate inhibits insulin-mediated glucose transport in mouse oxidative muscle. American Journal of Physiology. Endocrinology and Metabolism, 299(3), E364-73.

Laeger, T., Metges, C. C., & Kuhla, B. (2010). Role of β-hydroxybutyric acid in the central regulation of energy balance. Appetite, 54(3), 450-455.

CLAUSES

Clause 1. A compound, comprising:
a) β-hydroxybutyric acid (BHB); and
b) an ingestible and non-digestible weakly basic polymer, comprising monomers having weak base functional groups.

Clause 2. The compound according to Clause 1, wherein the molar ratio of BHB to the weak base monomer is about 1:1.

Clause 3. The compound of Clause 1 or 2, wherein the BHB is a racemic mixture.

Clause 4. The compound of Clause 3, wherein the BHB is greater than 50% of the D-isomer.

Clause 5. The compound of Clause 4, wherein the BHB is D-BHB.

Clause 6. The compound of any one of Clause 1 to 5, wherein the weakly basic polymer has a pKb of between about 4 to about 10.5.

Clause 7. The compound of any one of Clauses 1 to 6, wherein the weakly basic polymer is sodium-carboxymethylcellulose or chitosan.

Clause 8. The compound of Clause 1 wherein the compound has the formula

wherein x is an integer between about 2 and about 1000.

Clause 9. The compound of Clause 1, wherein the weakly basic polymer has the formula

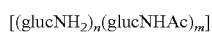

wherein
(glucNH$_2$) is a glucosamine residue,
(glucNHAc) is an N-acetylglucosamine residue;
"m" ranges from 0% to about 30% of the total residues;
"n" ranges from 70% to about 100% of the total residues;
wherein the total number of residues is between about 2 to about 1000, Clause 10. The compound of Clause 9, wherein the polymer has a mass of between about 9 kD to about 300 kD.

Clause 11. The compound of Clause 9, wherein the compound has the structure:

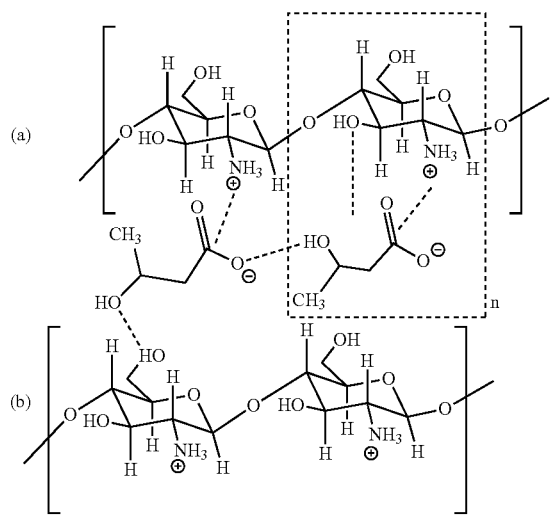

Clause 12. The compound of Clause 9, wherein the weakly basic polymer has the formula

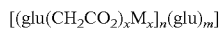

wherein

[glu(CH$_2$CO$_2$)$_x$M$_x$] are carboxymethyl glucose residues, glu are glucose residues;

x=1 or 2 or 3 and M are cations with charge, +1 or +2 or +3;

"m" ranges from 0% to about 30% of the total residues;

"n" ranges from 70% to about 100% of the total residues;

wherein the total number of residues is between about 2 to about 1000.

Clause 13. The compound of Clause 12, wherein the polymer has a mass of between about 9 kD to about 300 kD.

Clause 14. The compound of Clause 12, wherein the compound has the structure

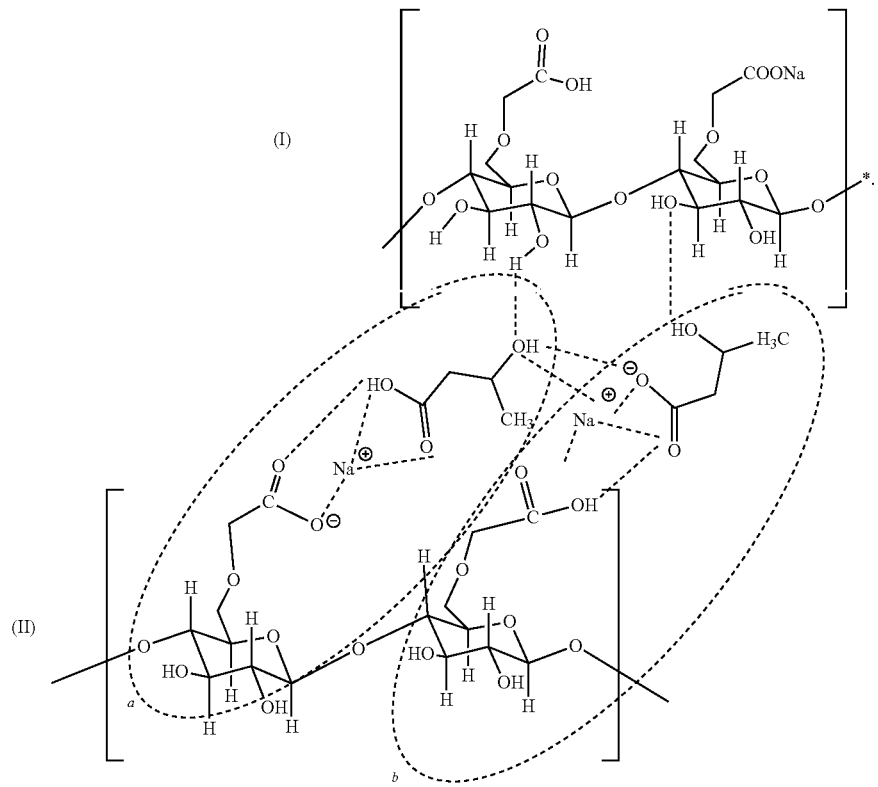

Clause 15. The compound of any one of Clauses 1 to 14, wherein the BHB has an intolerable taste and the compound is substantially free of the intolerable taste.

Clause 16. The compound of Clause 15, wherein the concentration of the BHB in a solution is at least about 1.0% (weight/volume).

Clause 17. A hydrogel comprising,
c) β-hydroxybutyric acid (BHB);
d) an ingestible and non-digestible weakly basic polymer, comprising monomers having weak base functional groups; and
e) water,
wherein the molar ratio of BHB to the weak base functional group is about 1:1.

Clause 18. The hydrogel of Clause 15, wherein the hydrogel further comprises additional ketogenic precursors.

Clause 19. The hydrogel of Clause 17, wherein the ketogenic precursor is poly-BHB, oligomers of BHB, 1,3-butanediol, and/or acetoacetic acid or esters thereof.

Clause 20. The hydrogel of Clause 17, further comprising additional BHB.

Clause 21. The hydrogel of Clause 20, wherein the ratio of BHB to weak base functional groups is greater than 1 to 1.

Clause 22. The hydrogel of Clause 21, wherein the ratio of BHB to weak base functional groups is greater than about 2 to about 1.

Clause 23. The hydrogel of Clause 22, wherein the ratio of BHB to weak base functional groups is greater than about 5 to about 1.

Clause 24. The hydrogel of Clause 23, wherein the ratio of BHB to weak base functional groups is greater than about 10 to about 1.

Clause 25. The hydrogel of any one of Clauses 17-24, wherein the BHB is D-BHB.

Clause 26. A method for increasing ketone levels comprising administering to a subject in need thereof a therapeutically effective amount of a compound as described in any one of Clauses 1 to 16, or a hydrogel as described in any one of Clauses 17 to 19, wherein BHB has an intolerable taste and the compound or hydrogel is substantially free of the intolerable-taste.

Clause 27. The method according to Clause 20, for promoting ketosis, for promoting weight loss or suppressing appetite, for preventing or treating neurodegenerative conditions, for preventing or treating traumatic brain injuries, for treating a condition caused by muscle impairment or muscle fatigue, for the prevention or the improvement of treatment for cancer, for treating diabetes, or for regulating or lowering blood glucose levels.

The invention claimed is:

1. A method for increasing ketone levels in the bloodstream of a subject comprising administering to the subject an aqueous composition comprising a hydrogel, the hydrogel comprising:
 a) β-hydroxybutyric acid (BHB); and
 b) chitosan having a mass of between about 9kD to about 300kD;
wherein the BHB and the chitosan form a hydrogel matrix, and the matrix has a pH in the aqueous composition of about 4.0±0.5.

2. The method of claim 1, wherein the BHB is a racemic mixture.

3. The method of claim 1, wherein the BHB is greater than 50% of the D-isomer.

4. The method of claim 1, wherein the BHB is D-BHB.

5. The method of claim 1, wherein the the chitosan comprises glucosamine residues, and the molar ratio of BHB to the glucosamine residues is about 1:1 (BHB:glucosamine residue).

6. The method of claim 1, wherein the chitosan comprises glucosamine residues, and the molar ratio of BHB to the glucosamine residues is greater than 1:1 (BHB:glucosamine residue).

7. The method of claim 6, wherein the molar ratio is about 2:1 (BHB:glucosamine residue).

8. The method of claim 6, wherein the molar ratio is about 5:1 (BHB:glucosamine residue).

9. The method of claim 6, wherein the molar ratio is about 10:1 (BHB:glucosamine residue).

10. The method of claim 1, wherein the hydrogel further comprises additional ketogenic precursors, which are selected from poly-BHB, oligomers of BHB, 1,3-butanediol, and acetoacetic acid or esters thereof.

* * * * *